United States Patent
Anantharamaiah

(12) 
(10) Patent No.: US 6,506,880 B2
(45) Date of Patent: Jan. 14, 2003

(54) SYNTHETIC PEPTIDES THAT ENHANCE ATHEROGENIC LIPOPROTEIN UPTAKE AND LOWER PLASMA CHOLESTEROL

(75) Inventor: Gattadahalli M. Anantharamaiah, Birmingham, AL (US)

(73) Assignee: The UAB Research Foundation, Birmingham, AL (US)

(*) Notice: Subject to any disclaimer, the term of this patent is extended or adjusted under 35 U.S.C. 154(b) by 0 days.

(21) Appl. No.: 09/520,698

(22) Filed: Mar. 7, 2000

(65) Prior Publication Data

US 2002/0128175 A1 Sep. 12, 2002

Related U.S. Application Data

(63) Continuation-in-part of application No. 09/271,066, filed on Mar. 17, 1999, now abandoned.
(60) Provisional application No. 60/078,229, filed on Mar. 17, 1998.

(51) Int. Cl.$^7$ .......................... C07K 17/00; A61K 38/00
(52) U.S. Cl. ........................ 530/359; 530/326; 530/328; 514/2; 514/12; 514/13; 514/15
(58) Field of Search .................................. 530/359, 326, 530/328; 514/2, 12, 13, 15

(56) References Cited

U.S. PATENT DOCUMENTS 5,473,039 A * 12/1995 Dyer et al. .................. 530/324

OTHER PUBLICATIONS

Cheung et al., *Journal of Lipid Research*, vol. 37, pp. 1099–1112, 1996.*

* cited by examiner

*Primary Examiner*—Christopher S. F. Low
*Assistant Examiner*—Abdel A. Mohamed
(74) *Attorney, Agent, or Firm*—Hale and Dorr LLP; Jane M. Love

(57) ABSTRACT

The present invention provides novel synthetic apolipoprotein E (ApoE)-mimicking peptides wherein the receptor binding domain of apolipoprotein E is covalently linked to 18A, the well characterized lipid-associating model class A amphipathic helical peptide. Such peptides enhance low density lipoprotein (LDL) and very low density lipoprotein (VLDL) binding to and degradation by fibroblast or HepG2 cells. Also provided are possible applications of the synthetic peptides in lowering human plasma LDL/VLDL cholesterol levels, thus inhibiting atherosclerosis.

19 Claims, 11 Drawing Sheets

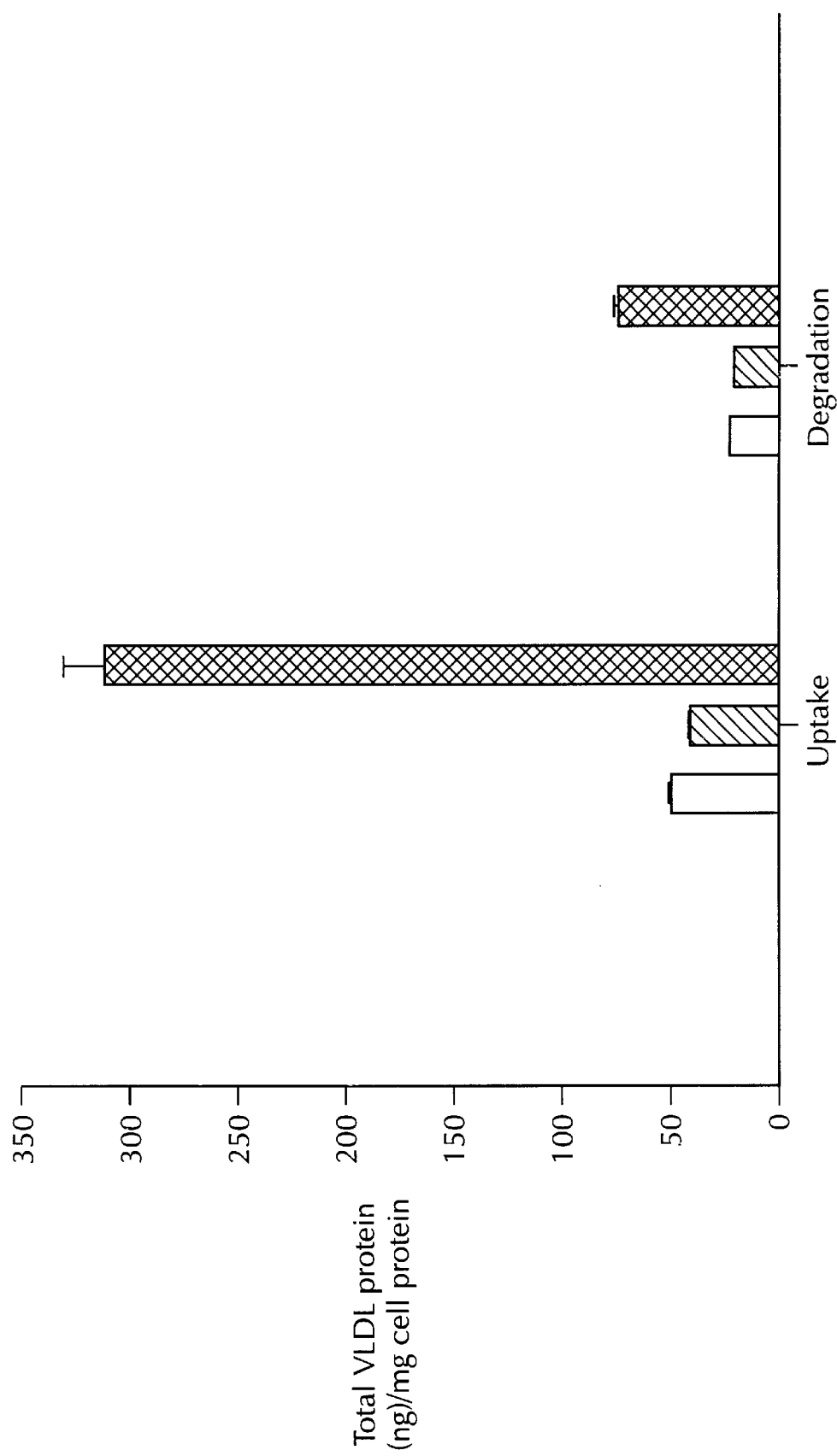

SEQUENCE LISTING

```
<160> NUMBER OF SEQ ID NOS: 10

<210> SEQ ID NO 1
<211> LENGTH: 10
<212> TYPE: PRT
<213> ORGANISM: Homo sapiens
<220> FEATURE:
<221> NAME/KEY: DOMAIN
```

-continued

```
<222> LOCATION: 141..150
<223> OTHER INFORMATION: minimal arginine-rich human apolipoprotein E
      receptor binding domain

<400> SEQUENCE: 1

Leu Arg Lys Leu Arg Lys Arg Leu Leu Arg
                5                   10

<210> SEQ ID NO 2
<211> LENGTH: 10
<212> TYPE: PRT
<213> ORGANISM: Mus sp.
<220> FEATURE:
<221> NAME/KEY: DOMAIN
<222> LOCATION: 133..142
<223> OTHER INFORMATION: mouse apolipoprotein E receptor binding domain

<400> SEQUENCE: 2

Leu Arg Lys Met Arg Lys Arg Leu Met Arg
                5                   10

<210> SEQ ID NO 3
<211> LENGTH: 10
<212> TYPE: PRT
<213> ORGANISM: Artificial Sequence
<220> FEATURE:
<223> OTHER INFORMATION: an analog of human apolipoprotein E receptor
      binding domain

<400> SEQUENCE: 3

Leu Arg Arg Leu Arg Arg Arg Leu Leu Arg
                5                   10

<210> SEQ ID NO 4
<211> LENGTH: 18
<212> TYPE: PRT
<213> ORGANISM: Unknown
<220> FEATURE:
<221> NAME/KEY: PEPTIDE
<223> OTHER INFORMATION: lipid-associating peptide

<400> SEQUENCE: 4

Asp Trp Leu Lys Ala Phe Tyr Asp Lys Val Ala Glu Lys Leu Lys
                5                   10                  15

Gly Ala Phe

<210> SEQ ID NO 5
<211> LENGTH: 10
<212> TYPE: PRT
<213> ORGANISM: Lepus sp.
<220> FEATURE:
<221> NAME/KEY: DOMAIN
<222> LOCATION: 134..143
<223> OTHER INFORMATION: rabbit apolipoprotein E receptor binding domain

<400> SEQUENCE: 5

Leu Arg Lys Leu Arg Lys Arg Leu Leu Arg
                5                   10

<210> SEQ ID NO 6
<211> LENGTH: 10
<212> TYPE: PRT
<213> ORGANISM: Monkey sp.
<220> FEATURE:
<221> NAME/KEY: DOMAIN
<222> LOCATION: 141..150
<223> OTHER INFORMATION: monkey apolipoprotein E receptor binding domain
```

-continued

```
<400> SEQUENCE: 6

Leu Arg Lys Leu Arg Lys Arg Leu Leu Arg
                 5                  10

<210> SEQ ID NO 7
<211> LENGTH: 10
<212> TYPE: PRT
<213> ORGANISM: Rattus sp.
<220> FEATURE:
<221> NAME/KEY: DOMAIN
<222> LOCATION: 133..142
<223> OTHER INFORMATION: rat apolipoprotein E receptor binding domain

<400> SEQUENCE: 7

Leu Arg Lys Met Arg Lys Arg Leu Met Arg
                 5                  10

<210> SEQ ID NO 8
<211> LENGTH: 10
<212> TYPE: PRT
<213> ORGANISM: Bovus sp.
<220> FEATURE:
<221> NAME/KEY: DOMAIN
<222> LOCATION: 140..149
<223> OTHER INFORMATION: bovine apolipoprotein E receptor binding domain

<400> SEQUENCE: 8

Leu Arg Lys Leu Pro Lys Arg Leu Leu Arg
                 5                  10

<210> SEQ ID NO 9
<211> LENGTH: 10
<212> TYPE: PRT
<213> ORGANISM: Porcus sp.
<220> FEATURE:
<221> NAME/KEY: DOMAIN
<222> LOCATION: 140..149
<223> OTHER INFORMATION: pig apolipoprotein E receptor binding domain

<400> SEQUENCE: 9

Leu Arg Asn Val Arg Lys Arg Leu Val Arg
                 5                  10

<210> SEQ ID NO 10
<211> LENGTH: 10
<212> TYPE: PRT
<213> ORGANISM: Canis sp.
<220> FEATURE:
<221> NAME/KEY: DOMAIN
<222> LOCATION: 133..142
<223> OTHER INFORMATION: dog apolipoprotein E receptor binding domain

<400> SEQUENCE: 10

Met Arg Lys Leu Arg Lys Arg Val Leu Arg
                 5                  10
```

SYNTHETIC PEPTIDES THAT ENHANCE ATHEROGENIC LIPOPROTEIN UPTAKE AND LOWER PLASMA CHOLESTEROL

CROSS-REFERENCE TO RELATED APPLICATIONS

This application is a continuation-in-part of U.S. patent application Ser. No. 09/271,066 filed Mar. 17, 1999, now abandoned which claims benefit of provisional patent application U.S. Serial No. 60/078,229 filed Mar. 17, 1998, now abandoned.

BACKGROUND OF THE INVENTION

1. Field of the Invention

The present invention relates generally to the field of cardiovascular medicine. More specifically, the present invention relates to synthetic peptides that can rapidly lower plasma cholesterol through enhanced LDL and VLDL uptake and degradation by cells.

2. Description of the Related Art

Apolipoprotein E (apo E) plays an important role in the metabolism of triglyceride-rich lipoproteins, such as very low density lipoprotein (VLDL) and chylomicrons. Apolipoprotein E mediates the high affinity binding of apo E-containing lipoproteins to the low density lipoprotein (LDL) receptor (apo B, E receptor) and the members of its gene family, including LDL receptor related protein (LRP), very low density lipoprotein receptor (VLDLR) and the apoE2 receptor (apoE2R) (1). The putative and complex role of apo E in atherosclerosis has been emphasized by several observations: (i) mice that overexpress human apo E have lower levels of total plasma cholesterol levels (2), (ii) intravenous injection of human apo E into cholesterol-fed rabbits protects these animals from atherosclerosis (3), and (iii) loss of the apo E gene in mice produces spontaneous atherosclerosis (4) which is ameliorated when macrophage-specific apo E expression is reconstituted in apo E-deficient mice (5).

Apo E is secreted as a 299 amino acid residue protein with a molecular weight of 34,200. Based on thrombin cleavage of apo E into two fragments, a two domain hypothesis was initially suggested to explain the fact that the C-terminal region of apo E (192–299) is essential for its binding to hypertriglyceridemic VLDL and the N-terminal 22 kDa domain (1–191), binds to the LDLR (6). Additional physical-chemical characterization of the protein and its mutants have extended this concept and have shown that the region 192–211 binds to phospholipid while the amino terminal domain (1–191) is a globular structure that contains the LDL receptor binding domain in the H$ (130–166) helix (7). Studies with synthetic peptides (Sparrow et al.) and monoclonal antibodies pinpointed the LDL receptor binding domain of apo E between residues 129–169, a domain enriched in positively charged amino acids, Arg and Lys (8–11).

Further studies with synthetic peptides were used to characterize the structural features of the binding domain of apo E that mediates its interaction with the LDL receptor (10–12). Residues 141–155 of apo E, although containing the positively charged residues, did not compete for binding of LDL in a human skin fibroblast assay, but did so only as tandem covalent repeats [i.e. (141–155)$_2$]. N-acetylation of the [141–15512]$_2$ peptide, on the other hand, enhanced LDL binding to fibroblasts (13). The N-acetylated [141–155]$_2$ analog selectively associated with cholesterol-rich lipoproteins and mediated their acute clearance in vivo (13). Furthermore, these studies indicated that the prerequisite for receptor binding is that the peptides be helical (12). Enhanced LDL uptake and degradation were also observed (14) using synthetic peptides modified to increase lipid association by N,N-distearyl derivation of glycine at the N-terminus of the native 129–169 sequence of Apo E (14). Although LDL binding is mediated by the cationic sequence 141–155 of human Apo E, Braddock et al. (15) have shown that model peptides of the highly conserved anionic domain (41–60 of human Apo E) also modulate the binding and internalization of LDL to cell surface receptors. However, these peptides do not enhance LDL degradation.

Each of the peptides described above used some form of the natural apo E receptor binding sequence. The prior art is deficient in the lack of synthetic peptides that enhance LDL and VLDL uptake. The present invention fulfills this long-standing need and desire in the art.

SUMMARY OF THE INVENTION

All of the peptides synthesized in the prior art studies mentioned above made use of the natural apo E sequence. With a view to designing a peptide with minimal structural features of apo E for receptor binding, two essential properties of apo E were incorporated: 1) a lipid binding domain at the C-terminus of the designed peptide, and 2) the receptor binding domain 141–150 from the human apo E sequence at the N-terminus. It was hypothesized that since lipid binding is essential for surface localization of the peptide on lipoproteins and for the receptor binding domain of apo E to be appropriately accessible to bind to the LDL receptor, joining a well-characterized, lipid-associating peptide such as the model class A amphipathic helix, 18A (16), to the 141–150 peptide sequence of apo E should be sufficient to confer biological activity.

A peptide LRKLRKRLLR-18A (hE-18A) is designed, in which LRKLRKRLLR (SEQ ID No. 1) is the 141–150 region of human apo E and 18A is a class A amphipathic helical peptide that associates with phospholipids and lipoprotein surfaces (17). To characterize the role of individual amino acid residues in the peptides several additional analogs were prepared. The receptor binding domain of apo E, LRKLRKRLLR, is well conserved in several species (Table 1). A peptide with the mouse apo E sequence, LRKMRKRLMR-18A (mE-18A, SEQ ID No. 2), where two conserved Leu in hE-18A were changed to Met, was also synthesized. To determine whether the receptor binding is sequence or charge specific, an analog, LRRLRRRLLR-18A (hE(R)-18A, SEQ ID No. 3) was synthesized. The sequences of these peptides are shown in Table 2.

TABLE 1

Receptor Binding Domain of ApoE in Different Species

| Species | Starting Residue no. | Sequence |
|---|---|---|
| Human | 141 | LRKLRKRLLR (SEQ ID No. 1) |
| Rabbit | 134 | LRKLRKRLLR (SEQ ID No. 5) |
| Monkey | 141 | LRKLRKRLLR (SEQ ID No. 6) |
| Mouse | 133 | **LRK*M*RKRL*M*R** (SEQ ID No. 2) |
| Rat | 133 | **LRK*M*RKRL*M*R** (SEQ ID No. 7) |
| Bovine | 140 | LRKLPKRLLR (SEQ ID No. 8) |
| Pig | 140 | **LR*NV*RKRL*V*R** (SEQ ID No. 9) |
| Dog | 133 | *M*RKLRKRV*L*R (SEQ ID No.10) |

The *italicized* residues indicate changes from the human sequence, however, the property of the amino acid is conserved. The bold-italicized residues indicate the difference in properties compared to the human sequence at that position.

TABLE 2

The Lipid Binding and the Receptor Binding Domains Used

| Lipid Binding Domain | | |
|---|---|---|
| 18 A | DWLKAFYDKVAEKLKGAF (SEQ ID No. 4) | |

| Receptor Binding Domain | | Peptides Made |
|---|---|---|
| HE | LRKLRKRLLR (SEQ ID No. 1) | hE-18A |
| ME | LRKMRKRLMR (SEQ ID No. 2) | mE-18A |
| H(R) | LRRLRRRLLR (SEQ ID No. 3) | h(R)-18A |

The above three peptides were end protected using acetyl and amino groups.

In addition, two-domain peptides were synthesized which were N-terminally protected since Ac-18A-NH$_2$ was previously shown to be more helical with a higher lipid affinity for phospholipids than the free peptide (16). The properties of these N-terminally protected peptides were compared with Ac-18A-NH$_2$, a peptide studied previously (17, 18), as a control peptide. The present invention describes their lipid-associating properties and the effect of these peptides on LDL and VLDL binding to and degradation in HepG2 cells.

Thus, the present invention is directed to the physical-chemical properties and the effects of these peptides on human LDL and VLDL binding and degradation. The studies demonstrate that these dual-domain peptides have unusual ability to bypass the LDLR pathway and the LRP receptor pathway and enhance dramatically the rapid uptake of LDL/VLDL by a cellular pathway that involved heparan sulfate proteoglycan. This peptide-enhanced LDL/VLDL uptake pathway suggests an alternate pharmacological route for LDL/VLDL cholesterol lowering independent of expression of LDLR family members.

In one embodiment of the present invention, there is provided a synthetic apolipoprotein E-mimicking peptide comprising a receptor binding domain of apolipoprotein E covalently linked to a lipid-associating peptide. Preferably, the lipid-associating peptide is model class A amphipathic helical peptide 18A. Further, it is preferable that the synthetic peptide is N-terminally protected using acetyl and amino groups.

In another embodiment of the present invention, the receptor binding domain of apolipoprotein E has an amino acid sequence selected from the group consisting of SEQ ID Nos. 1–3 and apolipoprotein E is from species selected from the group consisting of human, mouse, rabbit, monkey, rat, bovine, pig and dog.

In still another embodiment of the present invention, the synthetic apolipoprotein E-mimicking peptide both enhances LDL/VLDL binding to cells and increases LDL/VLDL degradation by cells, e.g., by cells such as hepatocytes.

In still another embodiment of the present invention, there is provided a method of using the synthetic apolipoprotein E-mimicking peptide to rapidly reduce circulating plasma cholesterol in vivo.

In yet another embodiment of the present invention, there is provided a pharmaceutical composition comprising a synthetic apolipoprotein E-mimicking peptide and a pharmaceutically acceptable carrier.

The present invention is further directed to applications of the pharmaceutical composition disclosed herein in enhancing LDL/VLVL binding to a cell, increasing LDL/VLDL degradation by a cell, lowering LDL/VLDL cholesterol in an in-need individual o r treating an individual with atherosclerosis by administering to the cell or individual with a pharmacologically effective dose of the pharmaceutical composition. Preferably, the effective dose is from about 0.01 mg/kg to about 100 mg/kg.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 9 shows uptake and degradation of $^{125}$IVLDL alone and $^{125}$I-VLDL-Ac-hE18A-NH$_2$ complex by Hep G2 cells. Ac-hE18A-NH$_2$ was used as a control. $^{125}$I-VLDL was incubated with Ac-hE18A-NH$_2$ (1:1 w/w) and reisolated by density centrifugation. The peptide bound to $^{125}$I-VLDL floated to the top while the unbound peptide was at the bottom. The $^{125}$I-VLDL-peptide complex was used to determine the effect of the peptide on the uptake and degradation of $^{125}$I-VLDL. The first bar: $^{125}$I-VLDL alone; the second bar: $^{125}$VLDL-Ac-18A-NH$_2$ (1:1 w/w); the third bar: VLDL-Ac-hE18A-NH$_2$ (1:1 w/w). The data represent an average of triplicate values.

FIG. 10 shows the effect of intravenously administered peptide on plasma lipoproteins. Female apo E knockout mice were injected through the tail vein with $^{125}$I-Ac-hE18A-NH$_2$ (50 μg in 100 μl PBS). Blood samples were taken by retro-orbital bleeding at baseline (0 h) and at 2 minutes and 6 hours following injection. Success of injection was determined by measuring radioactivity in the 2 minutes sample and calculating total plasma peptide by specific radioactivity of the peptide, assuming total plasma volume=4.2% of body weight.

DETAILED DESCRIPTION OF THE INVENTION

Figure 2:
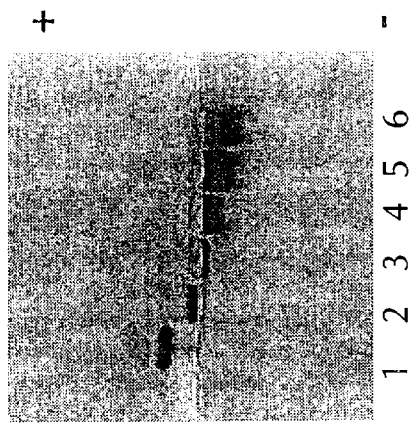
FIG. 2 shows agarose gel (0.7%) of LDL (10 µg) and LDL(10 µg) incubated with different concentrations of hE18A. The gel was stained with Coomassie Blue. Lanes: 1. LDL(10µg), 2. LDL+hE18A(1 µg), 3. LDL+hE18A(2.5 µg), 4. LDL+hE18A(5 µg), 5. LDL+hE18A(10 µg), 6. hE18A(10 µg).

Human apolipoprotein E (apo E) consists of two distinct domains, the lipid-associating domain (residues 192–299) and the globular domain (1–191) which contains the LDL receptor binding site (residues 129–169). To test the hypothesis that a minimal arginine-rich apoE receptor binding domain (141–150) is sufficient to enhance low density lipoprotein (LDL) and very low density lipoprotein (VLDL) uptake and clearance when covalently linked to a class A amphipathic helix, a peptide in which the receptor binding domain of human apo E, LRKLRKRLLR (hApo E[141–150], SEQ ID No. 1), is linked to 18A, a well characterized high affinity lipid-associating peptide (DWLKAFYDKVAEKLKEAF, SEQ ID No. 4) to an synthesize the peptide hApoE[141–150]-18A (hE18A) and its end protected analog, Ac-hE18A-NH$_2$. The importance of lysine residues and the role of the hydrophobic residues in the receptor binding domain were also studied using two analogs, LRRLRRRLLR-18A (hE(R)18A) and LRKMRKRLMR-18A (mE18A). The effect of the dual character peptides on the uptake and degradation of human LDL/VLDL by cells was determined.

In MEF 1 cells with induced LDL receptors, LDL internalization was enhanced three, five and seven times by Ac-mE18A-NH$_2$, Ac-hE18A-NH$_2$, and Ac-hE(R)18A-NH$_2$ respectively. All three peptides increased degradation of LDL by 100 percent. Both Ac-hE18A-NH$_2$ and the control peptide Ac-18A-NH$_2$ interacted with VLDL to cause a displacement of apo E from VLDL. However, only Ac-hE18A-NH$_2$-associated VLDL enhanced the uptake of VLDL six fold and degradation three fold compared to VLDL alone in spite of the absence of apo E. The LDL binding to fibroblasts in the presence of these peptides was not saturable, however, over the LDL concentration range studied.

Furthermore, a similar enhancement of LDL internalization was observed independent of the presence of the LDL receptor related protein (LRP) or LDL receptor or both. Pretreatment of cells with heparinase and heparitinase however abolished greater than 80% of enhanced peptide-mediated LDL uptake and degradation by cells. The data indicate that the dual-character peptides enhanced LDL uptake and degradation by binding to the LDL through the amphipathic lipid binding domain (18A). However, the minimal 141–150 Arg-rich domain did not confer receptor binding activity to the model peptide, but instead directed the LDL-peptide complex to the HSPG pathway for uptake and degradation by fibroblasts.

In one embodiment of the present invention, there is provided a synthetic apolipoprotein E-mimicking peptide comprising a receptor binding domain of apolipoprotein E covalently linked to a lipid-associating peptide. Preferably, the lipid-associating peptide is model class A amphipathic helical peptide 18A. Still preferably, the synthetic peptide is N-terminally protected using acetyl and amino group.

In another embodiment, the present invention is directed to the receptor binding domain of apolipoprotein E has an amino acid sequence selected from the group consisting of SEQ ID Nos. 1–3 and apolipoprotein E is from species selected from the group consisting of human, mouse, rabbit, monkey, rat, bovine, pig and dog.

In still another embodiment, the present invention is directed to a synthetic apolipoprotein E-mimicking peptide that both enhances LDL/VLDL binding to cells and increases LDL/VLDL degradation by cells.

In still another embodiment of the present invention, there is provided a method of using the synthetic apolipoprotein E-mimicking peptide to rapidly reduce circulating plasma cholesterol in vivo.

In yet another embodiment, the present invention is directed a pharmaceutical composition comprising the synthetic apolipoprotein E-mimicking peptide and a pharmaceutically acceptable carrier.

The present invention is further directed to applications of the pharmaceutical composition disclosed herein in enhancing LDL/VLDL binding to a cell, increasing LDL/VLDL degradation by a cell, lowering LDL/VLDL cholesterol in an in-need individual or treating an individual with atherosclerosis by administering to the cell or individual with a pharmacologically effective dose of the pharmaceutical composition. Preferably, the effective dose is from about 0.01 mg/kg to about 100 mg/kg.

The following examples are given for the purpose of illustrating various embodiments of the invention and are not meant to limit the present invention in any fashion.

EXAMPLE 1

Synthesis of the Peptides

Peptides were synthesized using the solid phase method and Fmoc chemistry, and a peptide synthesizer from Protein Technology, according to the procedure described previously (19). The peptide resin was subjected to HF cleavage to ensure the complete removal of the 4-methoxy-2,3,6-trimethylbenzenesulfonyl (Mtr) group from Arg residues. For the cleavage of peptides from the resin, Trp, mercaptoethanol and dimethyl sulfide were used as scavengers and for the cleavage of mE-18A, Met, Trp, mercaptoethanol and dimethylsulfide were used as scavengers. The cleaved peptides were purified on a preparative C-4 reversed-phase HPLC column and purity was determined by C-18 analytical reversed phase HPLC and confirmed by mass spectral analysis.

EXAMPLE 2

Preparation of LDL/VLDL and Lipoprotein Deficient Serum (LPDS)

Plasma LDL was prepared by sequential density ultracentrifugation (20) using human plasma obtained from the Red Cross. VLDL was removed by centrifuging plasma (density of 1.006 g/ml) at 50000 rpm in a 50Ti Sorvall rotor for 18 h. The density of he VLDL deficient plasma was adjusted to 1.063 g/ml with potassium bromide and centrifuged at 50000 rpm to obtain LDL. The LDL (1.006–1.063 g/ml) was washed with 150 mM NaCl by overlayering and recentrifuging and dialyzed exhaustively against 150 mM NaCl containing 0.24 mM EDTA. Purity of the LDL fraction was determined by Superose 6 (Pharmacia, Inc) column chromatography and by agarose electrophoresis.

Similarly, plasma VLDL was prepared from human plasma by sequential centrifugation using density ultracentrifugation (20). The VLDL (1.006 g/ml) was isolated by centrifuging plasma at 50,000 rpm at 4° C. for 24 h and washed by reisolation. Purity of the VLDL fraction was determined by Superose 6 (Pharmacia, Inc) column chromatography and by agarose electrophoresis.

For preparation of LPDS, the density of plasma was adjusted to 1.21 g/ml with potassium bromide and centrifuged at 50,000 rpm at 4° C. for 24 h. The top fraction consisting of lipoproteins was removed. The lower fraction, which is devoid of lipoproteins, was dialyzed extensively against 150 mM NaCl at 4° C. for 60 h. The LPDS was sterilized by filtration through a 0.22$\mu$m Millipore filter.

EXAMPLE 3

$^{125}$I Labeling of LDL/VLDL and Peptides

LDL/VLDL or peptides were labeled with $^{125}$I using the method of Bilheimer et al (21). Briefly, LDL/VLDL or peptide solution was mixed with glycine buffer (1 M glycine, pH=10) at 200 $\mu$l glycine buffer per ml of LDL/VLDL or peptide solution. ICl solution (2 M NaCl and 0.5% ICl) was added at 3.2 $\mu$l per mg of protein. $^{125}$I (Amersham; carrier free in NaOH solution) was then added and the mixture immediately applied to a desalting column (BioRad; Econopak 10DG) which had been pre-equilibrated with the desired buffer. The $^{125}$I-labeled material was separated from free $^{125}$Iodine in 1 ml aliquots which were then counted to identify the labeled material. Peak fractions were pooled and specific activity determined.

EXAMPLE 4

Agarose Gel Electrophoresis

Agarose gel electrophoresis was carried out according to the procedure of Asztalos (22). LDL and the LDL-peptide mixture were electrophoresed on a 0.7% agarose gel. Tris-tricine buffer (25 mM, pH 8.6) was used for both gel and electrode buffers. Since the peptides are positively charged, the wells were made in the center of the gel to allow for movement in both directions. 2 $\mu$l samples (containing about 5 $\mu$g of LDL) were diluted with 2 $\mu$l of Tris-tricine buffer containing 10% glycerol and bromophenol blue. Samples were eletrophoresed at a constant voltage of 250 volts for about 2 h or until the dye reached the top of the gel. After the run, the gel was stained with Coomassie blue. In order to determine the stoichiometry of binding, $^{125}$I-labeled peptides were used and the stained bands were excised and counted to determine the ratio of peptide to LDL.

EXAMPLE 5

Binding, Internalization, and Degradation of LDL/VLDL by Mouse Embryonic Fibroblasts and Hep G2 Cells The binding, internalization and degradation of LDL/VLDL in fibroblasts were measured using the method of Goldstein et. al. (20). All cells were grown in DMEM medium in 6-well plates and used at 75–90% confluence was reached. The seeding density of cells used was between $1.5 \times 10^5$ and $3.0 \times 10^5$ cells/ml medium. Cells were incubated with DMEM medium containing LPDS 24 hours prior to use to upregulate LDL receptors. The cells were then incubated with indicated concentrations (0 $\mu$g–50 $\mu$g) of $^{125}$I -LDL/$^{125}$I-VLDL at 4° C. for 2 hours in the presence or absence of peptides. Non-specific binding was determined in the presence of 50 fold excess unlabelled LDL/VLDL with or without peptides. After washing with ice cold PBS (containing BSA 2 mg/ml), to remove excess free labeled lipoprotein, the cells were incubated with dextran sulfate (4 mg/ml, Pharmacia, $M_r$ 500,000) or heparin (Sigma Chemical Co., 10 mg/ml) for 1 h to release spcifically bound $^{125}$I-LDL/$^{125}$I-VLDL, and washed with cold PBS. The counts in the dextran sulfate wash reflect the amount of LDL/VLDL bound to cells.

The cells were dissolved in 0.1 N NaOH and a 0.5 ml aliquot of cell suspension was counted. These counts reflect the amount of LDL/VLDL internalized. Protein was estimated by the method of Lowry. Degradation of LDL/VLDL were studied using the protocol described above for 4° C., except that the cells were incubated at 37° C. for 5 hours. Degradation was determined by precipitating the unbound $^{125}$I-LDL/$^{125}$I-VLDL from the medium with 50% TCA (0.5 ml of 50% TCA was added to 1 ml of medium) and incubating at 4° C. for 30 minutes (20). The precipitate was removed by centrifugation. The supernatant was treated with 10 µl of 40% potassium iodide and 40 µl of 30% hydrogen peroxide. The free $^{125}$I liberated was extracted with 2 ml of chloroform. The upper aqueous layer (0.5 ml) was then counted. This represented the amount of $^{125}$I-monoiodotyrosine produced by the degradation of apoB in LDL/VLDL.

Heparinase and heparitinase treatment of cells was carried out as follows. The cells were treated with heparinase and heparitinase (Sigma Chemical Co.) at a concentration of 3 U/ml of media for 2 hours at 37° C. These experiments were carried out using human and mouse fibroblasts as well as HepG2 cells. Mouse embryonic fibroblasts (MEF1), the LRP deficient mutant (PEA13) and the LRP/LDL double mutant (MEF4) were (obtained from ATCC ) used to identify the possible mechanism involved. In all the cell experiments, the average value of triplicates was used.

EXAMPLE 6

Circular Dichroic Spectrometry

Circular dichroic spectra were recorded on a signal averaging AVIV 62DS spectropolarimeter as described earlier (18). Briefly, circular dichroic spectra were obtained at 25° C. by signal averaging of four scans recorded every nm from 260 nm to 190 nm using a cell with a 0.01 cm path length Peptide concentrations in PBS, pH 7.4, used were 100 µM. Peptide-DMPC complexes (1:20 m/m) were prepared as described (18) and the change in peptide helicity upon lipid association measured. The helical content of the peptides was estimated from the mean residue ellipticity, $[\theta]_{MRE}$ (deg.cm$^2$.dmol$^{-1}$) at 222 nm using the equations as detailed by Morrisett et al.(23).

EXAMPLE 7

Purity and Secondary Structure of the Peptides

Peptide purity was determined by HPLC analysis and confirmed by mass spectral analyses. Each peptide is helical in PBS and each increases its helicity in the presence of DMPC (Table 3). The increase in helicity in the presence of lipid is not as great as that observed for Ac-18A-NH$_2$ alone, suggesting that the addition of receptor binding domain does not extend the helix completely into this domain when the peptide is associated with a lipid surface. However, the hE18A and mE18A have 36% α helical content while hE(R)18A has a higher value (~50%). Protecting the end groups also increased the helicity of each peptide to an average value of 67% (Table 3). Addition of lipid to these peptides (peptide/lipid 1:20 m/m) increases the helicity to an average value 75% (Table 3). However, there was no significant difference in the helicities of the protected peptides in the free and the bound state.

TABLE 3

Percent Helicity of E-18A Analogs

| | Peptide | Peptide/DMPC (1:20) |
|---|---|---|
| hE-18A | 36.0 | 46.0 |
| mE-18A | 36.3 | 44.0 |
| hE-(R)18A | 51.2 | 70.8 |
| hB(K)18A | 34.6 | 48.4 |
| Ac-hE18A-NH2 | 69.3 | 74.3 |
| Ac-mE18A-NH2 | 67.8 | 77.3 |
| Ac-hE(R)18A-NH2 | 64.6 | 66.4 |

Figure 1:
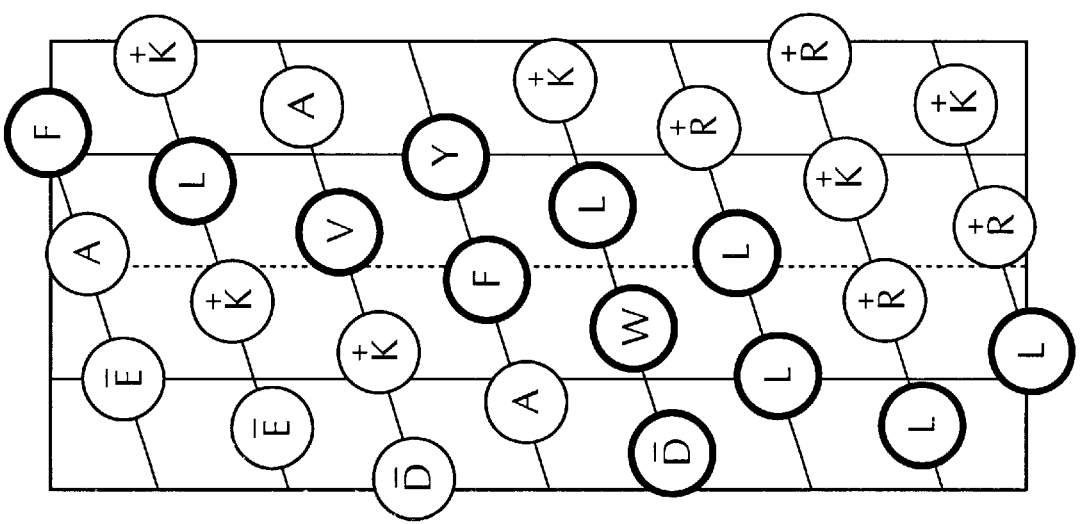
FIG. 1 shows helical net analysis of the peptides 18A and hE18A. The amino acids are shown in one letter code. The hydrophobic residues are in dark circles and the charges of the amino acids are also shown.

The helical net analyses of the E-18A sequence (FIG. 1) shows a continuous nonpolar face with a 180° C. twist. The hydrophobic amino acids present in the receptor binding domain appear to extend the nonpolar face of the amphipathic lipid-associating peptide 18A domain. All the positively charged residues from the receptor binding domain and one from 18A domain are located at the lower right hand corner of the helical net diagram suggesting a positive cluster that may be important for the LDL receptor. binding of apoE (24). The negatively charged residues are clustered in the upper left hand corner with adjacent positively charged residues. Thus hE18A has a localized net positive charge (arginine and lysine rich) that can bind to negative charges and a hydrophobic strip that can bind to lipids. An increase in helicity of the peptides would increase the localization of the positive charges that would enhance the ability of the peptide to bind to negatively charged molecules.

EXAMPLE 8

Intravenous Administration of Peptides

50 µg of the $^{125}$I-labeled peptide was injected into the tail vein into female apo E-gene knock out mice. Blood was drawn by retro-orbital bleeding immediately before injection (time 0), and at two minutes and 6 hours following the injection. Success of injections was determined by measuring the plasma radioactivity in the two minute sample; the total plasma peptide at two minutes was determined from the specific activity of the injected peptide and the radioactivity present in the plasma. Total plasma volume was assumed to be 4.2% of body weight. Plasma cholesterol profiles were determined on 5 µl of 0 h and 6 h samples by the CLiP method.

EXAMPLE 9

Column Cholesterol Lipoprotein Profiles (CLiP)

CLiP were determined using a modification of a previously described method for the semi-automated cholesterol profiling of lipoproteins by column chromatography (31). The apparatus consisted of two biocompatible HPLC pumps, an injector Pharmacia), a post-column reactor, a 30×1 cm Superose 6 column, and a spectrophotometric detector reading at 500 nm. Plasma samples were injected onto the Superose 6 column. Immediately after the column, cholesterol reagent (Cholesterol 1000, Pharmacia) was mixed with the column eluent through a low-dead-volume mixing tee, and the mixture entered a heating block (set at 550° C.). Outflow from the heating block entered the spectrophotometric detector, and the cholesterol profile was collected through an A/D board and the digitized profile stored in a computer.

EXAMPLE 10

Binding of the Peptides to LDL

Peptides were incubated at room temperature with LDL at various ratios for 1 h and then analyzed by agarose gel electrophoresis (FIG. 2). LDL can be seen as a single, homogenous band migrating toward the anode (lane 1) while the peptide (10 µg) appeared as a diffuse band migrating toward the cathode (lane 6). The anodic mobility of the LDL treated with peptide was retarded and the degree of retardation of mobility was dependent upon the ratio of peptide to LDL. At a peptide:LDL ratio of 2.5:10 (w/w), no free peptide was detected (FIG. 2, lane 3). However, at higher peptide concentrations (5:10 and 10:10 w/w), free peptide was detected (stained material moving toward the cathode, FIG. 2, lane 6). These results indicate that the peptide can associate with LDL. Similar results were also observed with other peptide analogs. Using $^{125}$I labeled Ac-hE18A-NH$_2$, the stoichiometry was determined to be 30 molecules of peptide to one of LDL (assuming one molecule of ApoB per LDL particle). Therefore, it appears that these peptides bind to LDL and modify its surface. The control peptide, Ac-18A-NH$_2$, since its net charge is zero, did not change the mobility of LDL.

EXAMPLE 11

Effect of the Peptides on LDL Uptake and Degradation

Figure 3A:
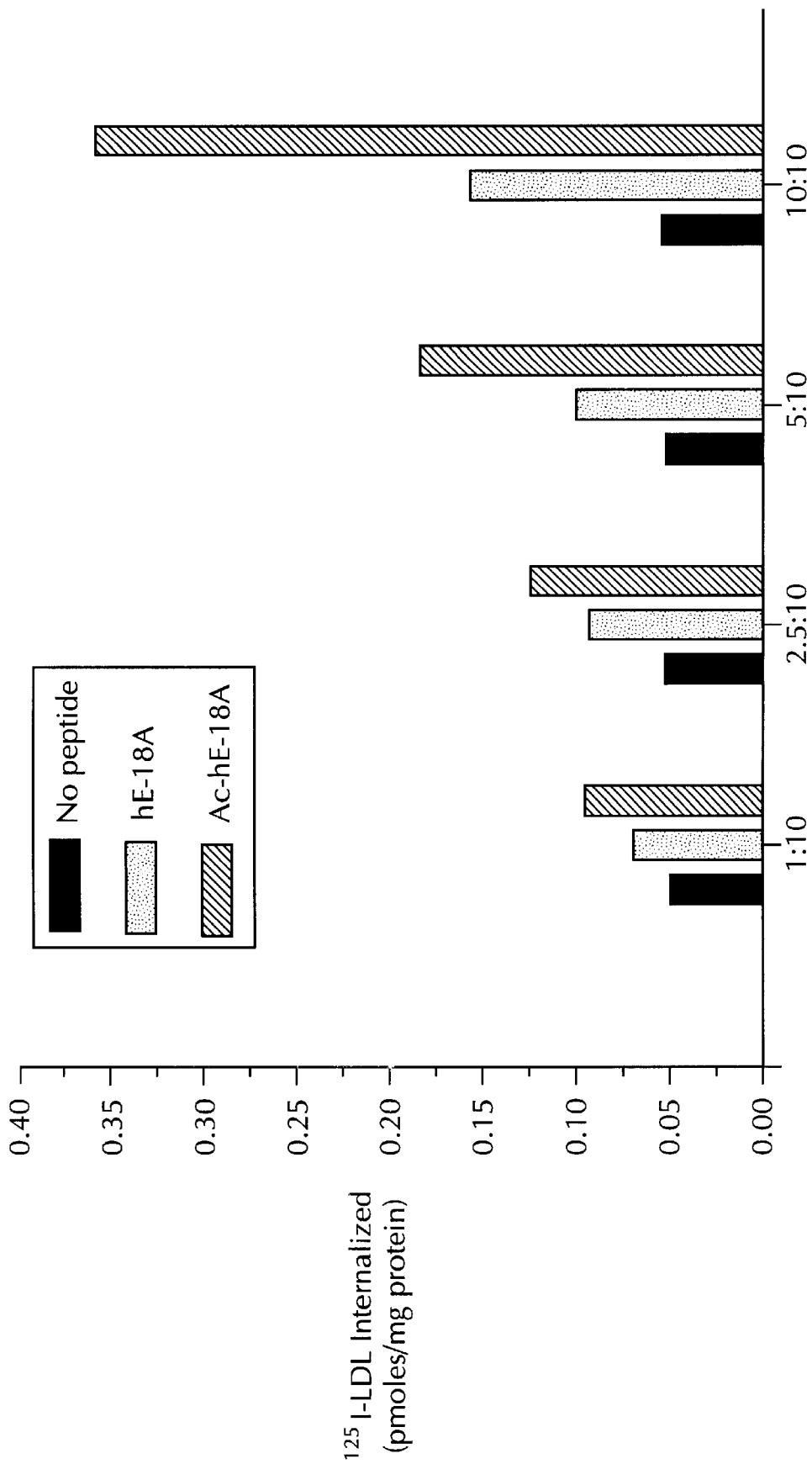
FIG. 3A shows the effect of different concentrations of hE18A and Ac-hE18A-NH$_2$ on the specific internalization of $^{125}$I-LDL in MEF1 cells. Cells were grown in DMEM in a monolayer in 6 well plates. $^{125}$I-LDL(10 µg) was incubated with different concentrations of peptides (1 µg to 10µg) at room temperature for 1 hour. This mixture was then incubated with the cells for 2 hours at 37° C. and the effect of the peptide on internalization of LDL was measured after 2 hours incubation at 37° C.

The peptides were designed to mimic apo E, containing the minimal LDL receptor binding domain as well as a lipid binding domain. These peptides were used to determine this potential impact on receptor mediated binding and uptake of LDL in mouse fibroblasts. At different concentrations (1–10 μg) of the petides, hE18A and Ac-hE18A-NH$_2$, with LDL constant at 10 μg (FIG. 3A) specific internalization of LDL was dependent on the concentration of peptide used. At the highest concentration (10 μg) used, Ac-hE18A-NH$_2$ was 5 times more effective than with hE18A. This was also true for the other analogs. However, the control peptide Ac-18A-NH$_2$, and the receptor binding region by itself (LRKLRKRLLR) did not enhance LDL uptake (results not shown).

These results suggest that both the lipid binding domain (Ac18ANH$_2$) and the receptor binding domain, when covalently linked possess a structure suitable for binding to the LDL surface. Since protected peptides, with increased helicity enhance binding and uptake much more (≈5 times) than the corresponding free peptides, increased helicity appears to increase the uptake due to a clustering of positive charges. The positively charged cluster is formed only in the helical form of the peptide suggesting that the overall conformation of the peptide is responsible for the increased uptake of LDL in presence of these peptides. Since the protected peptides were more active in promoting the uptake of LDL, further experiments were carried out with the protected peptides.

Figure 3B:
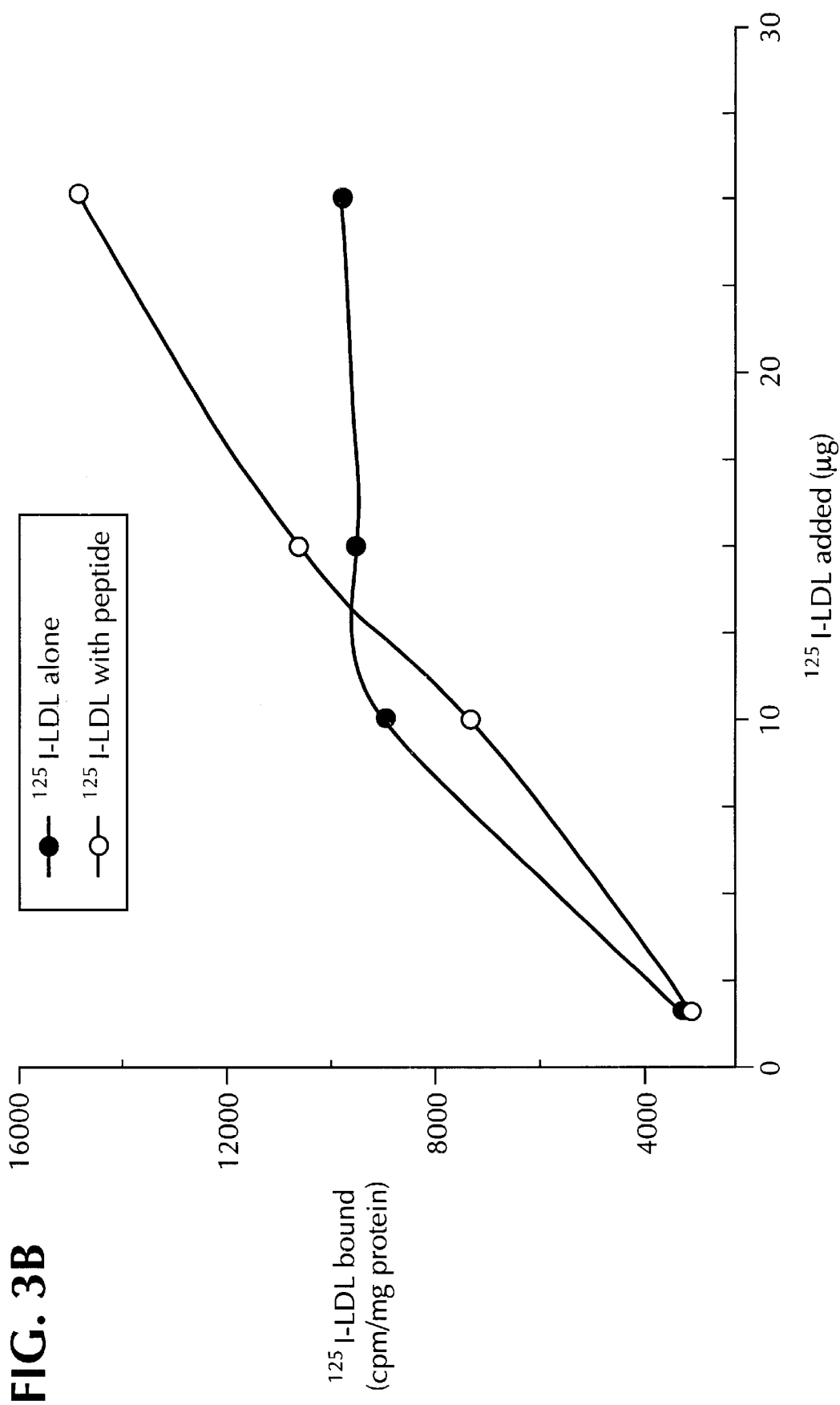
FIG. 3B shows binding of $^{125}$-LDL to MEF1 cells as a function of LDL concentration. Filled circles represent LDL without peptide and open circles represent LDL in presence of the peptide. The saturation in LDL binding that is observed in the absence of the peptide is abolished by the peptide.

Internalization of $^{125}$I-LDL was studied at increasing concentrations of LDL (from 1 μg to 25 μg per ml) (FIG. 3B) keeping the peptide concentration constant at 10 μg/ml medium. In the absence of peptide, saturation binding is observed at 10 μg/ml, whereas in the presence of peptide no saturation is observed, suggesting that LDL maybe taken up in a receptor-independent pathway.

Figure 4:
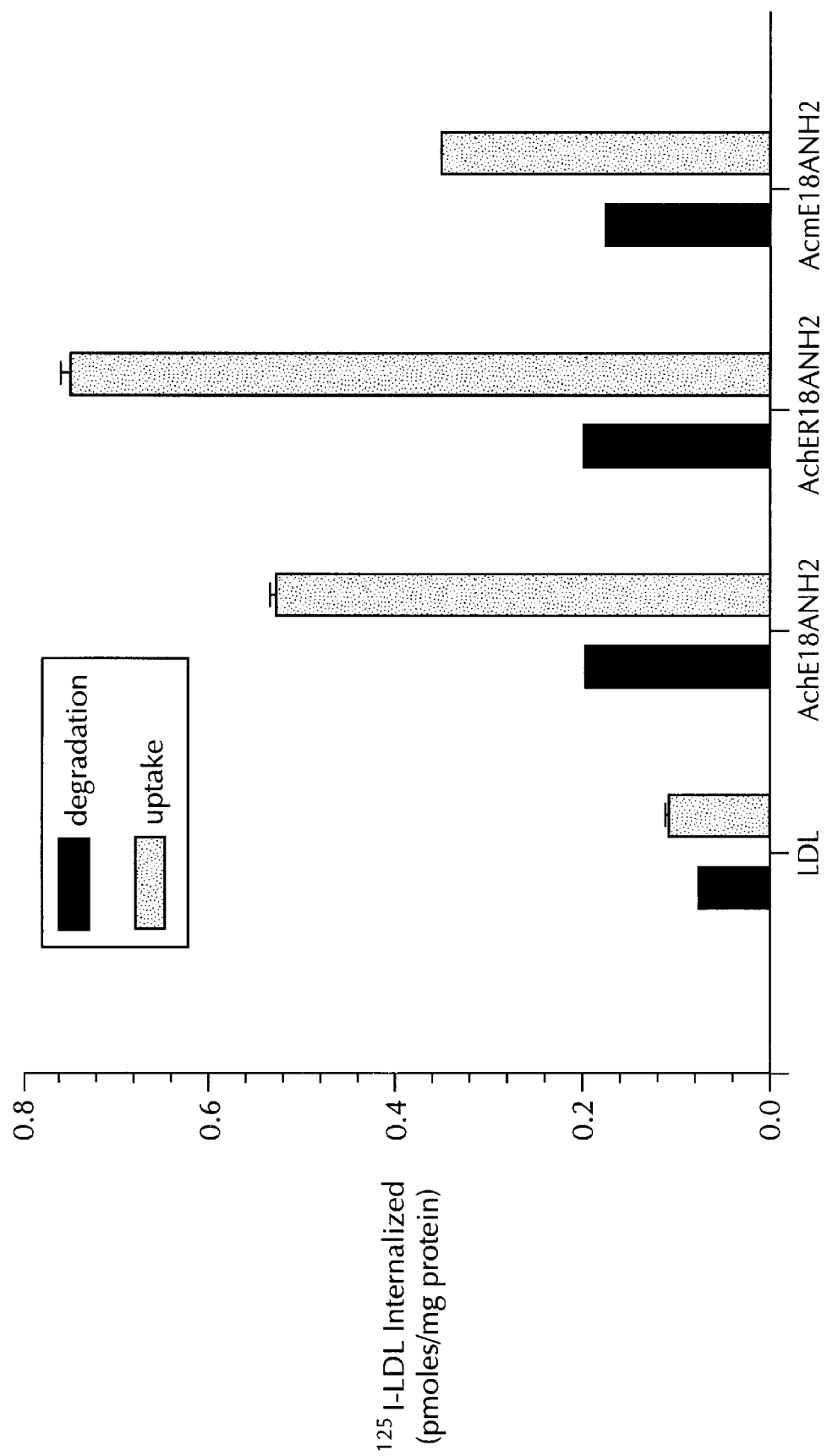
FIG. 4 shows internalization and degradation of $^{125}$-LDL (10 µg) in the presence of 10 µg Ac-hE18A-NH$_2$, Ac-hE(R) 18A-NH$_2$, and Ac-mE18A-NH$_2$. The MEF1 cells were grown and treated with $^{125}$I-LDL-peptide and internalized was studied after a 2 hours incubation of cells at 37° C., while degradation was measured after incubating cells for 5 hours at 37° C. The black bars represent degradation and the speckled bars represent internalization.

The effect of the peptide was studied in two ways: (a) the peptide was added to the cell media directly after adding LDL and (b) it was first incubated with LDL for 1 h at room temperature and the coincubated mixture was added to the cells after filtering through a 0.221μ filter. The peptide-LDL "complex" or modified LDL appears to enhance the uptake of $^{125}$I-LDL much more than the peptide by itself (results not shown). An enhancement of seven, five and three times for internalization was observed for Ac-hE(R) 18A-NH$_2$, Ac-hE18A-NH$_2$, and Ac-mE18A-NH$_2$ respectively (FIG. 4). Although the three peptides are similar and they all "bind" to LDL in a similar manner, the nature of the amino acid residues does seem to play a role in the uptake and degradation of LDL to the fibroblasts. Substituting two hydrophobic Leu residues with the hydrophobic Met (Ac-mE18A-NH$_2$) did enhance internalization, although to a lesser extent than Ac-hE18A-NH$_2$. On the other hand, substitution of the two Lys residues with Arg increased the internalization by the peptide even though the cluster of positive charges was maintained. These results show that it is not just the charge or the hydrophobicity that is important but that the nature of the residue plays a role in determining its ability to internalize LDL, possibly because of their contribution to the helicity of the peptide.

The peptides also enhance degradation of LDL in these cells (FIG. 4). Even though they enhance internalization of LDL to different amounts, they all enhance the degradation of LDL to the same extent, approximately 2-fold. It is possible that the degradation reflects the LDL being internalized through the receptor dependent pathway but this is not so since ligand blots showed that the peptide-LDL complex does not bind to the LDL receptor.

ApoE mediates the uptake of lipoproteins through the LDLR family pathways (1, 25, 26). However, since the uptake in presence of the peptide was not saturable the results suggest that the LDL-peptide 'complex' was taken up through an alternate receptor-independent pathway. To determine the role of the LDL and LRP receptors in the enhanced peptide mediated uptake of LDL, the internalization of LDL-peptide 'complex' in LRP deficient (LRP-/-) cells and in LDL and LRP deficient cells (LDL-/- and LRP-/-) was studied.

Figure 5:
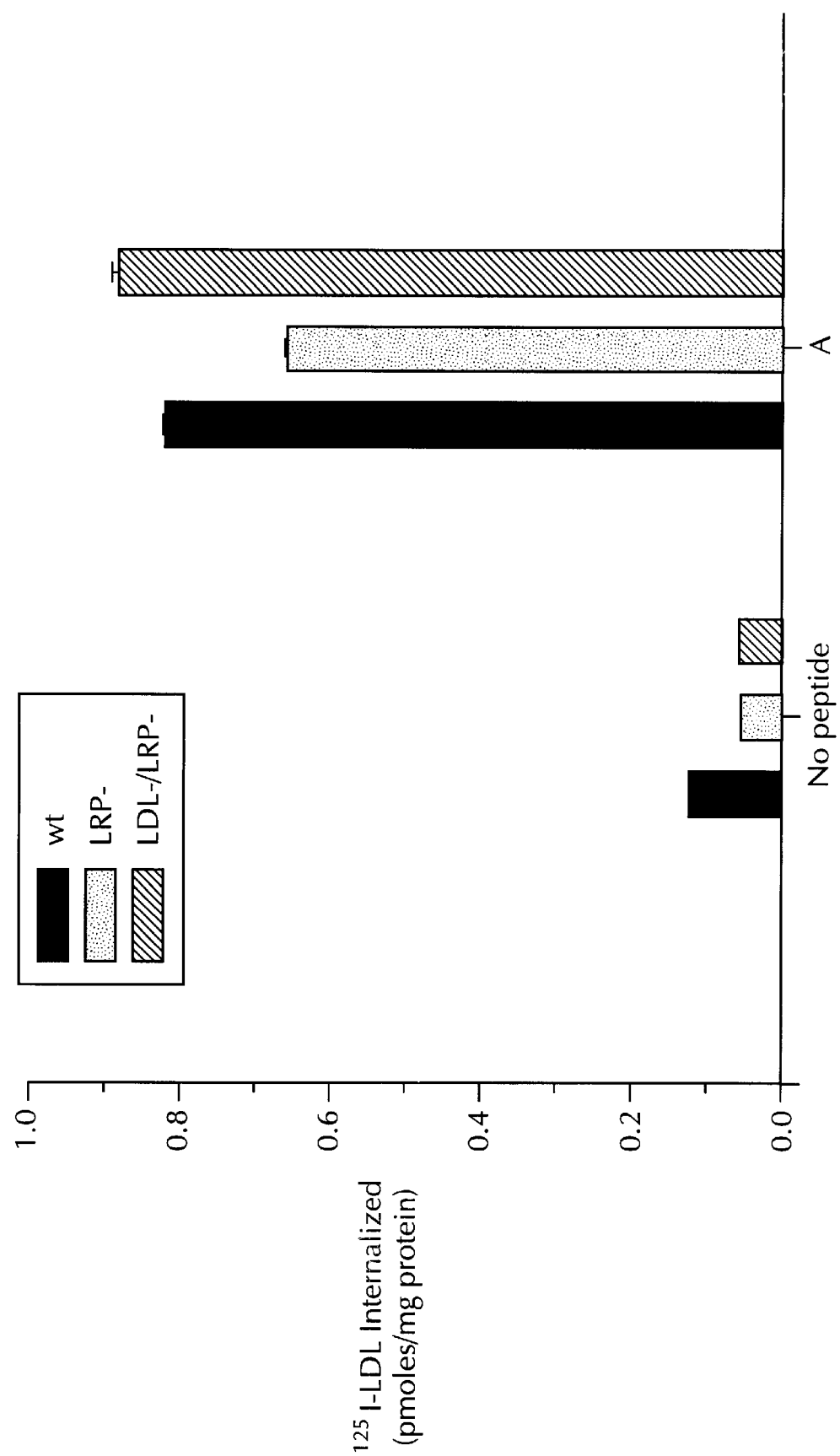
FIG. 5 shows a comparison of the specific internalization of $^{125}$I-LDL (10 µg) after coincubation with 10 µg of Ac-hE18A-NH2 for 1 hour at room temperature in wild type and LRP(−)/LRP(−) and LDL(−) mouse embryonic fibroblasts. $^{125}$I-LDL and peptide were coincubated for 1 h at room temperature and then filtered with a 0.221µfilter and incubated with the cells for 2 hours at 37° C. The black bars represent wild type cells (MEF1), the speckled bars represent LRP(−) cells and the striped bars the LRP(−)/LDL(−) cells.

The uptake of LDL in the presence of the peptides w as similar in all three cell types (FIG. 5), suggesting that the LDL-peptide 'complex' was neither being taken up through the LDL receptor pathway nor through the LRP pathway. Ligand blots indicated no enhanced LDL receptor binding with LDL preincubated with the (results not shown), further corroborating that LDL was internalized through a pathway independent of LDL and LRP receptors.

Figure 6:
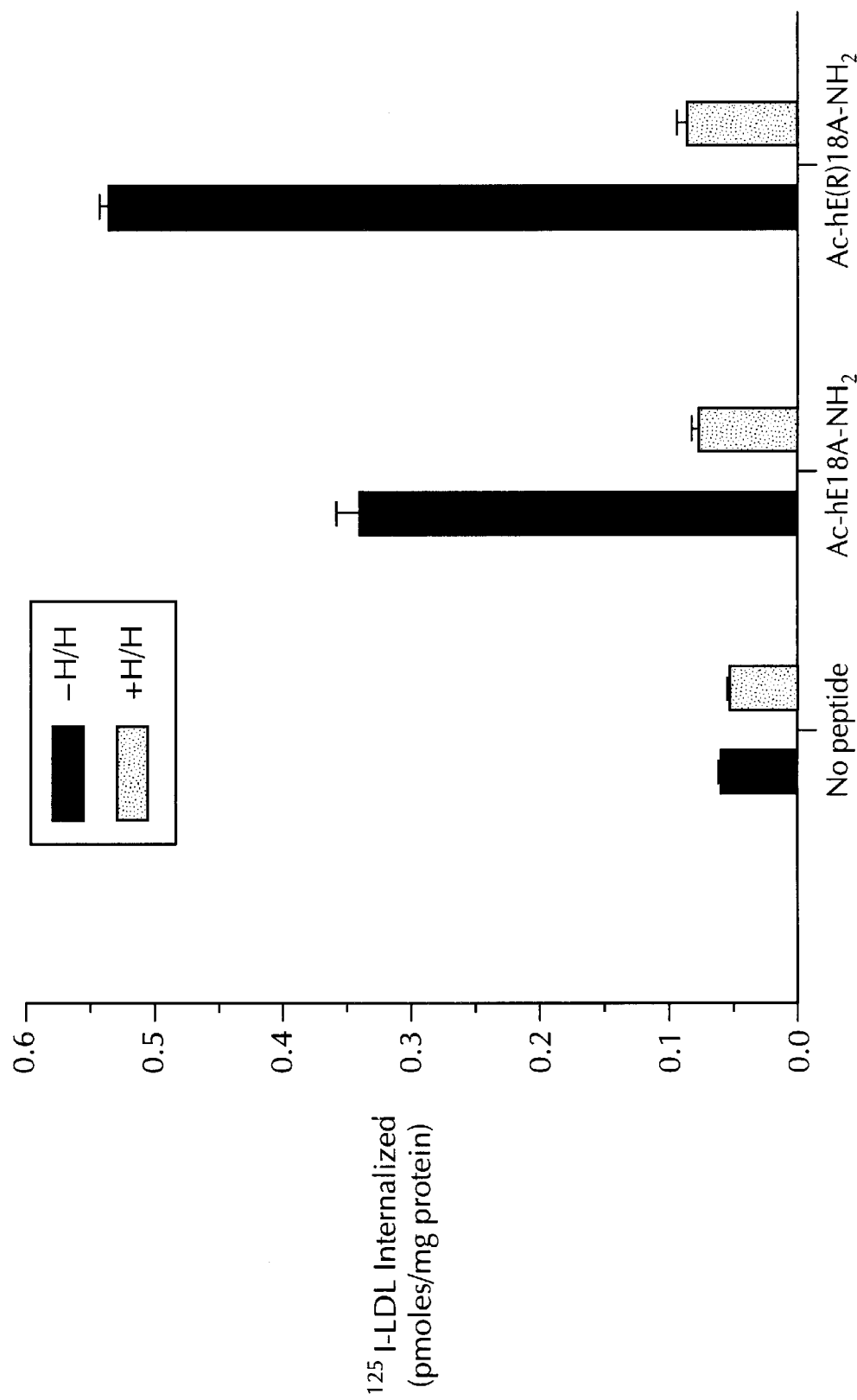
FIG. 6 shows the effect of heparinase/heparitinase on the internalization of $^{125}$I-LDL (10 µg) after incubating with Ac-hE18A-NH$_2$ (10 μg) for 1 h at room temperature. MEF1 cells were pretreated with heparinase/heparitinase(3U/ml) for 2 hours at 37° C. and then incubated with $^{125}$1I-LDL-peptide for 2 hours at 37° C. The black bars represent internalization without heparinase/heparitinase treatment while the speckled bars represent internalization after pretreatment with heparinase/heparitinase.

A possible high capacity, low affinity pathway has been previously identified for lipoprotein binding and uptake. Heparan sulfate proteoglycans (HSPG) bind and take up apo E-enriched lipoproteins (27). The receptor binding domain of apoE has been shown to coincide with the heparin binding domain (28). These apo E mimicking peptides could modify LDL and be taken up through heparan sulfate proteoglycans. Therefore, the cells were treated with heparinase and heparitinase (0.5 units each/ml). These enzymes have been shown to act on the cell surface heparan sulfate proteoglycans and inhibit the uptake of apo E enriched remnant lipoproteins (27, 29). Treatment of MEF1 cells with heparinase/heparitinase did not affect the internalization of LDL (FIG. 6) but the uptake of peptide treated LDL was reduced by almost 50% for the Ac-hE18A-NH$_2$ treated cells and by about 40% for the Ac-hE(R)18A-NH$_2$ treated cells. Increasing the concentrations of heparinase and heparitinase (0.5 U/ml to 3 U/ml) gradually decreased the observed enhancement (results not shown) till at 3U/ml it was totally abolished (FIG. 6), suggesting that the HSPG pathway is the major pathway for the peptide mediated internalization of LDL.

Nikoulin and Curtis (13) have shown that a modified dimer of the receptor binding domain binds to LDL and increases LDL binding to fibroblasts. The increase in the the peptide-mediated uptake of these peptides appears to be via the LRP and the HSPG pathway. However, it is not clear whether this N-acetylated dimer peptide increases degradation of LDL. Comparison of peptide:LDL stoichiometry obtained by the dimer peptides of Nikoulin and Curtis (13) (5 molecules of peptide per LDL) and the E-18A peptides reported in this study (30 molecules of peptide per LDL)

indicate enhanced binding of the E-18A peptides to LDL surface. This could be due to the presence of the lipid binding domain, 18A. This increased binding could be responsible for the enhanced degradation that was observed.

The anionic peptide used by Braddock et al. (15) also bound LDL and increased LDL binding by 6–7 times, in LDL receptor negative fibroblasts. However, degradation was only 10% of that in LDL receptor positive cells. Moreover, this peptide was active in both LRP/LDL deficient cells as well as in cells treated with heparinase, implicating a pathway different from the ones observed by the peptides of LDL described herein. These two studies with two totally different peptides, one anionic and one cationic (13, 15) suggest that even though they both bring about an increase in LDL uptake in cells, they do not increase degradation and also that the pathways responsible for internalization in all three cases are different. The peptides, on the other hand, increase internalization and degradation in cells. The lipid binding region therefore appears to be playing a major role in internalization. Apo E binds preferentially to larger lipoproteins. It is suggested that by changing the lipid binding domain (the hydrophobic nature and or the length) of these apo E mimetic peptides, peptides could be designed to target other lipoproteins and effect a greater internalization of these.

In summary, the present invention demonstrates that if the apo E-receptor binding domain, which is also a receptor binding domain, is able to associate strongly with LDL, this is sufficient to increase the LDL binding to cells. These peptides are able to enhance both internalization and degradation. This enhancement appears to be through the heparan sulfate proteoglycans pathway. Since LDL degradation is correlated to decreased LDL plasma cholesterol, these studies thus open the possibility of decreasing plasma LDL with these peptides. Finally, since a transgenic mouse model can be produced for a model synthetic peptide (30), it will be interesting to express this peptide in an apo E knockout mouse model and study the effect of the expressed peptide on spontaneously-developed atherosclerosis that is seen in apoE knock out mice (4). These studies are therefore important in designing apo E-mimicking peptides that can be easily synthesized and potentially be used for therapeutic intervention of atherosclerosis.

EXAMPLE 12

Peptides Bind to VLDL Surface and Displace apo E

Figure 7:
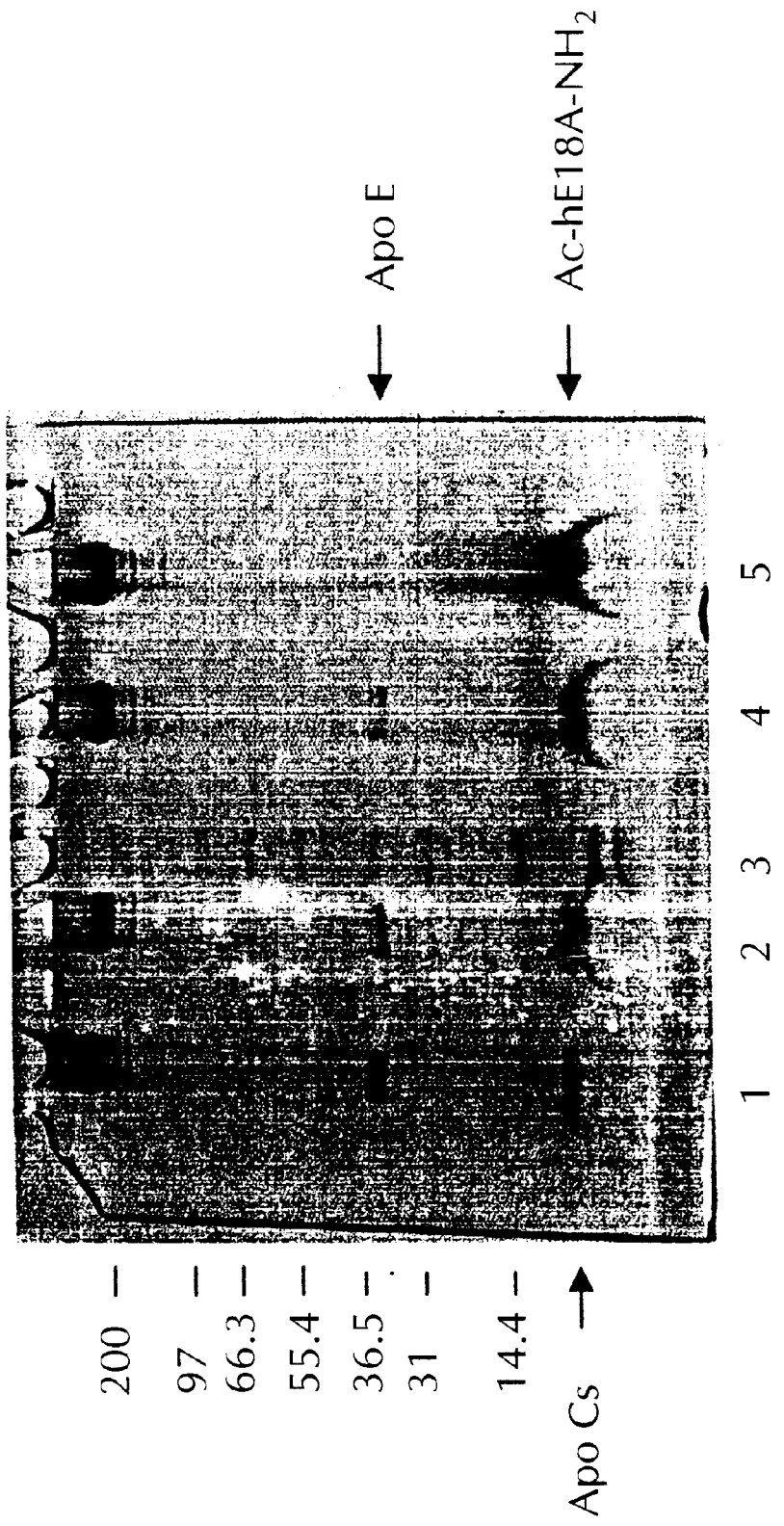
FIG. 7 shows SDS PAGE (10–20%) of apolipoproteins in VLDL and VLDL-Ac-hE18A-NH$_2$ complexes reisolated by density centrifugation. The gel is stained with Coomassie Brilliant blue. Lanes: 1: VLDL alone; 2: VLDL-Ac-hE18A-NH$_2$ (1:0.15 w/w); 3: Molecular weight standards; 4: VLDL-Ac-hE18A-NH$_2$ (1:0.3 w/w); 5: VLDL-Ac-hE18A-NH$_2$ (1:0.6 w/w). The positions of the apolipoproteins and the peptide are clearly marked. The numbers indicate the molecular weights of the standards. Each of the lanes contains the same amount of VLDL. The decrease in the amount of apo E with increasing concentration of peptide is evident.

VLDL was incubated with increasing concentrations of the peptide at the weight ratios indicated in the legend of FIG. 7 and the peptide-VLDL mixtures were subjected to density gradient ultracentrifugation to separate VLDL from free peptide. The apolipoprotein compositions of the reisolated VLDL-peptide complexes were examined by SDS-PAGE (FIG. 7). At equal VLDL particle concentration (determined by cholesterol concentration) the content of apo E relative to that of apo B was lower in peptide treated VLDL (lanes 2,4 and 5) than in VLDL alone (lane 1). It is evident that the decrease in apo E in VLDL is concomitant with the increase in peptide concentration. Negligible amounts of apo E were detectable in VLDL at the peptide:VLDL ratio of 0.6:1.0 (lane 5). The decrease in apo E with increasing amount of peptide indicates that apo E is displaced from VLDL by Ac-hE18A-NH$_2$. The effect of Ac-18A-NH$_2$ on VLDL has been described elsewhere (17) and has been shown to associate with the VLDL surface. The band corresponding to the peptide intensified with increasing concentration of the peptide, suggesting that with increasing concentration of the peptide, increasing amount of peptide associates with VLDL. The apo Cs have the same $R_f$ as the peptide. The effect of the dual-domain peptide on the apo Cs was established by immunoprecipitation as described below.

Figure 8:
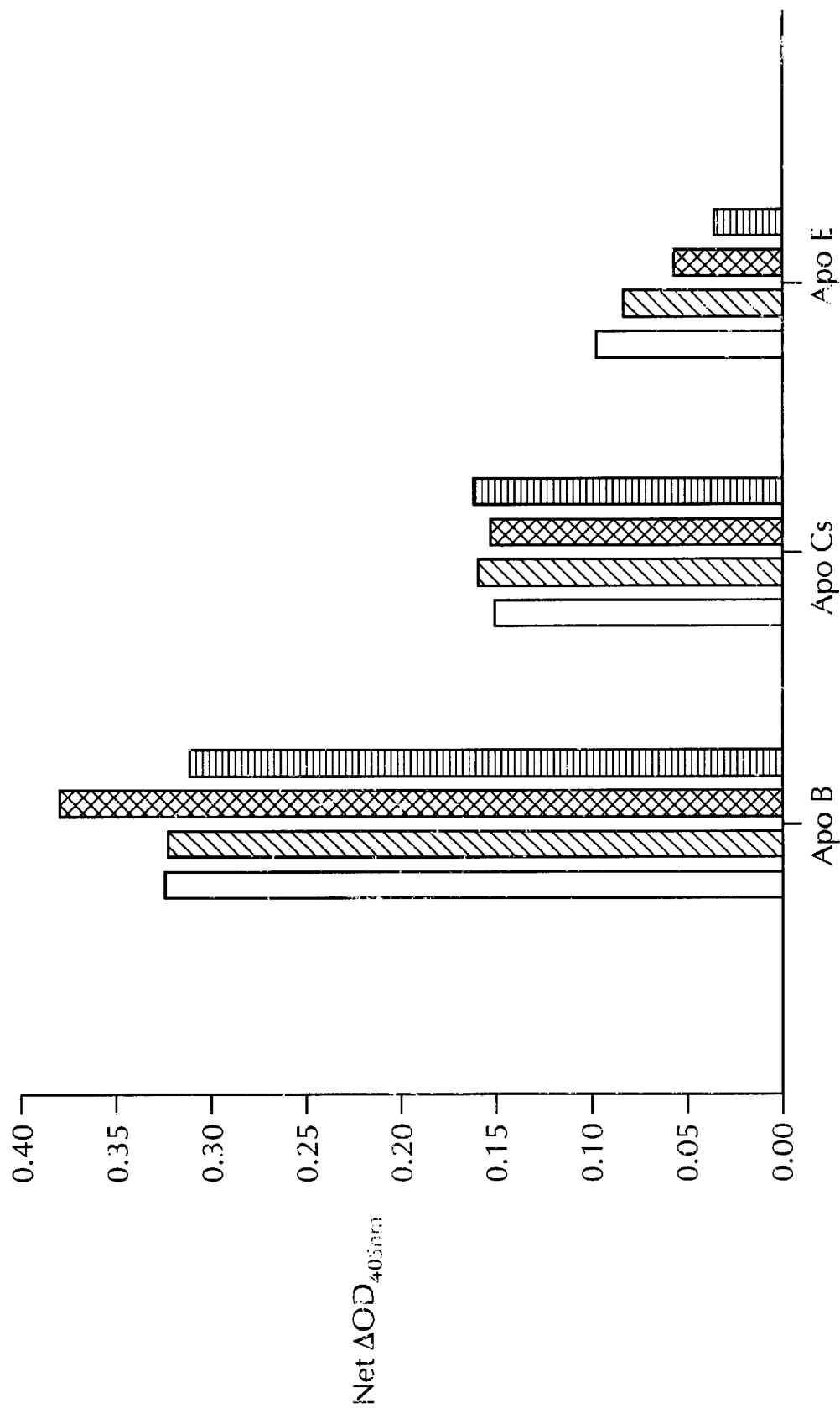
FIG. 8 shows immunoprecipitation of the apolipoproteins present on VLDL and VLDL-Ac-hE18A-NH$_2$ as a function of Ac-hE18A-NH$_2$ concentration. The VLDL and VLDL-Ac-hE 18A-NH$_2$ were treated with antibodies to apo B, apoCs, and apo E The apolipoproteins were thus precipitated and the resulting turbidity was measured at 405 nm. Turbidity was proportional to the amount of the apolipoprotein present on VLDL. The X-axis shows the apolipoproteins that were estimated viz. Apo B, Apo Cs and Apo E The first bar: VLDL alone; the second bar: VLDL-Ac-hE 18A-NH$_2$ (1:0.15 w/w); the third bar: VLDL-Ac-hE18A-NH$_2$ (1:0.3 w/w); the fourth bar: VLDL-Ac-hE18A-NH$_2$ (1:0.6 w/w).

The effect of this peptide on other VLDL proteins was also examined by immunoprecipitation of apo B, apo E and apo Cs. Antibodies specific to apo B, apo E and the apo Cs were used to precipitate the respective proteins from VLDL and the VLDL-Ac-hE18A-NH$_2$ complex. The resulting turbidity was a quantitative measure of the amount of protein present in VLDL after treatment with the peptide. Levels of apo B and apo C were not changed by the binding of Ac-hE18A-NH$_2$ while the levels of apo E were reduced (FIG. 8). Increasing concentration of peptide did not affect either apo B or apo C levels, while a concomitant decrease in apo E was apparent.

These results support the SDS PAGE results that the apo E mimetic peptide, Ac-hE18A-NH$_2$, is able to displace apo E from VLDL. At the VLDL:peptide ratio of 1:0.6, some amount of apo E was still observed to be present by immunoprecipitation, while Coomassie Brilliant blue staining of the SDS PAGE gel did not show any significant amount due to the sensitivity of the technique. Ac-18A-NH$_2$ also displaces apo E although not all the protein is displaced at the VLDL:peptide ratio of 1:0.6 (data not shown). These VLDL-peptide complexes (with small amounts of apo E) were used to study the effect of Ac-hE18A-NH$_2$ on the uptake of VLDL in vitro by HepG2 cells and in vivo in apo E-/- mice.

EXAMPLE 13

The Dual-domain Peptide but not the Class Amphipathic Helical Peptide Enhances VLDL Binding and Degradation in HepG2 Cells Ac-hE18A-NH$_2$ was designed to enable the incorporation of increased positively charged density on to the VLDL surface. Although a significant amount of apo E was displaced by both peptides, Ac-hE18A-NH$_2$ and Ac-18A-NH$_2$, VLDL containing Ac-hE18A-NH$_2$ was taken up by the HepG2 cells but not Ac-18A-NH$_2$-containing VLDL. The observed uptake of VLDL-Ac-hE18A-NH$_2$ (1:1 w/w on protein weight basis) by HepG2 cells was much more (six times enhancement) than that of VLDL alone. These results demonstrate that the addition of arginine-rich positively charged residues to the class A amphipathic peptide is sufficient to enhance the uptake of VLDL by HepG2 cells. Although both peptides, Ac-18A-NH$_2$ (17) and Ac-hE l8A-NH$_2$ displace apo E from VLDL to similar extent (FIGS. 7 and 8), only Ac-hE18A-NH$_2$ enhances the uptake by the HepG2 cells. Ac-18A-NH$_2$ does not increase uptake of VLDL, if anything, the uptake appears to be less than that of VLDL alone as would be expected with the loss of apo E, a known fact f or receptor-mediated binding to cells.

The observed enhanced uptake of VLDL-Ac-hE18A-NH$_2$ could be attributed to several possibilities: (i) changes in apo B structure; (ii) the presence of residual apo E and (iii) the unmasking of latent sites. The most likely mechanism is that since both peptides bind at equal levels and both displace the endogenous ligand apo E but only Ac-hE-18A-NH2 enhances uptake and degradation, the highly positively charged domain interacts with the cell surface to localize the peptide:lipoprotein complex, probably through HSPG as determined for LDL-peptide complex interactions in fibroblasts. In HepG2 cells, Ac-hE18A-NH$_2$ is able to not only enhance VLDL uptake by six times over the control, but also the degradation of VLDL by three times (FIG. 9). These results suggest that the peptide could clear plasma cholesterol in a hyperlipoprotenemic situation rapidly.

EXAMPLE 10

Ac-hE18A-NH$_2$ Rapidly Reduces Circulating Plasma Cholesterol in vivo

Figure 10A:
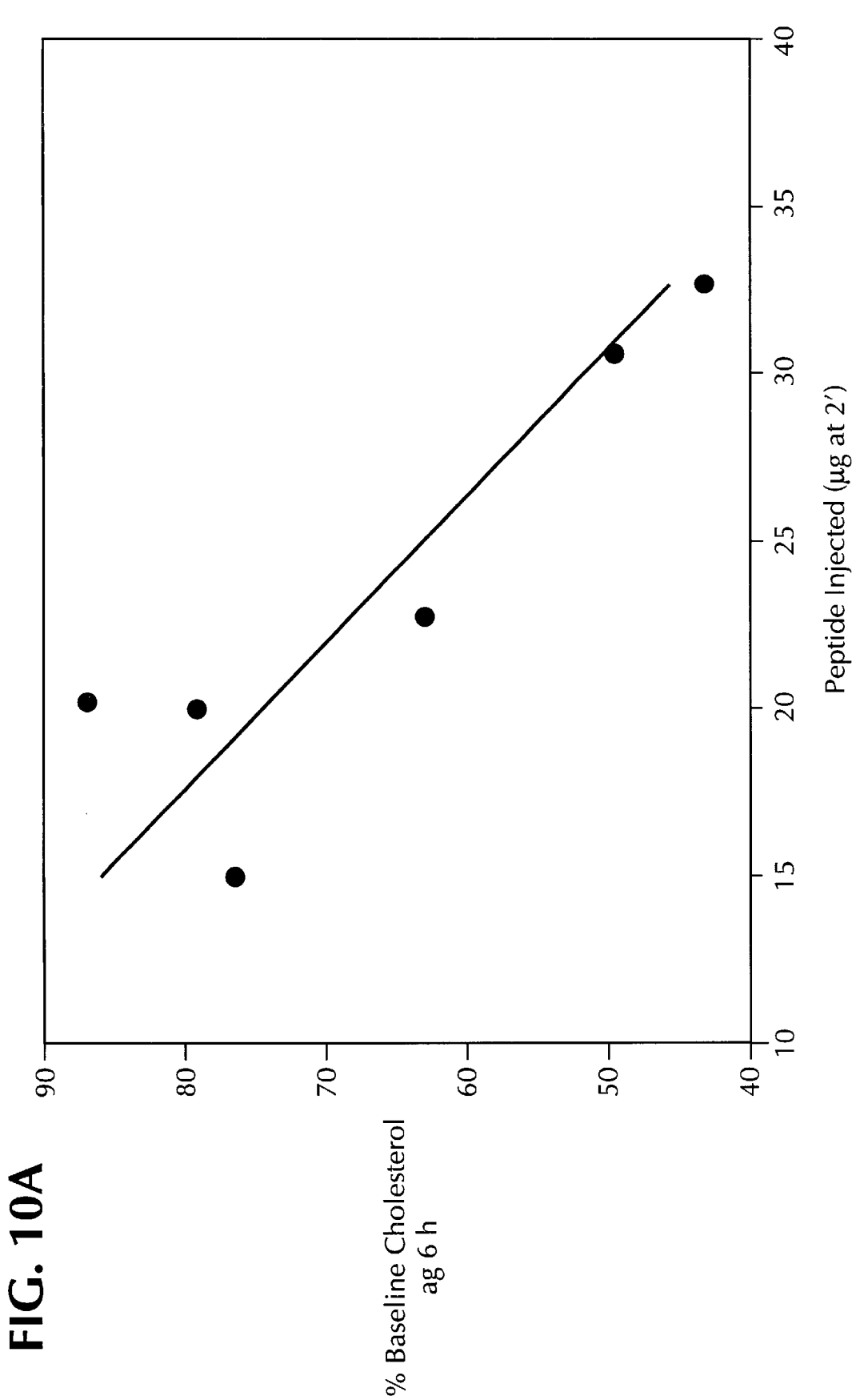
FIG. 10A shows the correlation of reduction in plasma cholesterol at 6 hours (as percent of baseline cholesterol) with injected peptide; ($r^2$=0.797, p<0.02).
Figure 10B:
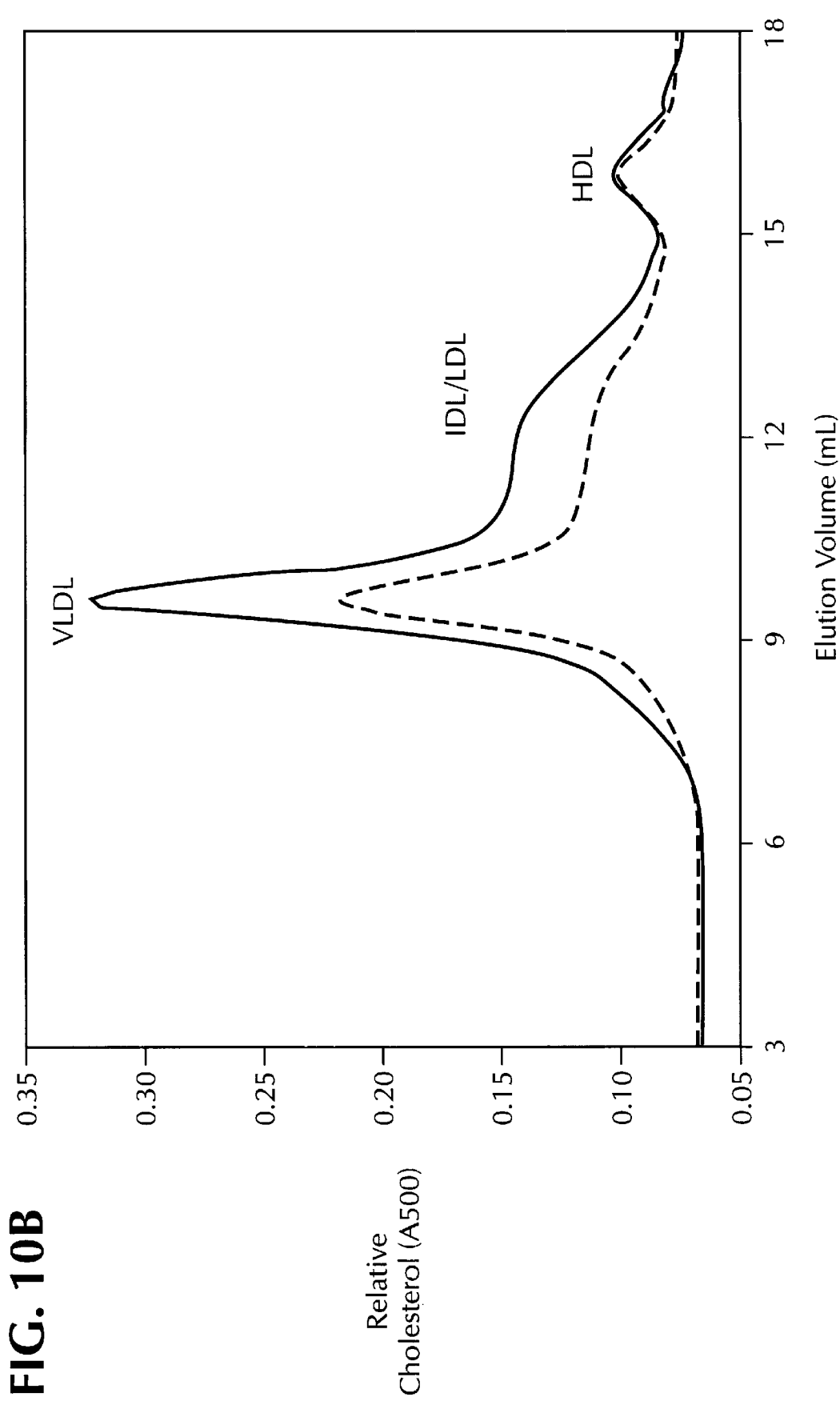
FIG. 10B shows plasma cholesterol profiles at baseline (solid line) and 6 hours following injection (dashed line) in a single animal (with total plasma peptide of 32.7 ug at 2 minutes following injection).

To determine the effect of peptide Ac-hE18A-NH$_2$ in clearing the plasma cholesterol, 14 μg to 33 μg of the peptide were administered into six apo E(-/-) animals. In every case, the plasma cholesterol levels decreased. Increased concentration of the peptide decreased more of plasma cholesterol (FIG. 10A) with minimum being 20% to a maximum of approximately 58% ($r^2$=0.797, p<0.02). FIG. 10B shows the plasma cholesterol profile of control apo E(-/-) and peptide administered (intravenous administration) apo E(-/-) mice. Total cholesterol was reduced by >50%. The most interesting fact to note, however, is that both VLDL and LDL cholesterol levels were lowered while HDL cholesterol was unchanged. These results are in agreement with earlier in vitro work where enhanced LDL uptake was seen.

Since 1% reduction in serum cholesterol is known to reduce the risk for cardiovascular diseases by 2%, the peptides have the potential to exert a substantial cardioprotective effect. The mechanism of this clearance can be further examined by using different gene knock out mice. Transgenic mice that are positive to peptide gene in apo E(-/-) mice can be generated to further establish the cardioprotective effect of this peptide. The enhanced clearance of VLDL would result in a significant reduction of plasma cholesterol since VLDL transports more cholesterol than LDL (five times that of LDL). Since this peptide appears to direct the uptake via a HSPG its effect would be of pharmacological importance in cases of subjects with structure/function defects in the LDLR.

The following references were cited herein.
1) Mahley, R. W., (1988) Science 240, 622–630
2) Shimono, H. N., et al., (1992) Eur. J. Clin. Invest. 90, 2084-2991.
3) Yamada, et al., (1989) Proc. Natl. Acad. Sci. U.S.A. 86, 665–669.
4) Zhang, S. H., et al., (1992) Science 258, 468–471.
5) Spangenberg, J., et al., (1997) Biochem. Biophys. Acta 1349, 109–121.
6) Bradley, W. A., et al., (1986) J. Lipid Res. 27, 40–48.
7) Wilson, C., et al., (1991) Science 252, 1817–1822.
8) Rall, S. C., Jr., et al., (1982) PNAS USA 79, 4696–4700.
9) Lalazar, A., et al., (1988) J. Biol. Chem. 263, 3542–2545.
10) Dyer, C. A., et al., (1991) J. Biol. Chem. 296, 22803–22806.
11) Dyer, C. A., et al., (1991) J. Biol. Chem. 266, 15009–15015.
12) Dyer, C. A., et al., (1995) J. Lipid Res. 36, 80–88.
13) Nicoulin, I. R., et al., (1998) J. Clin Invest. 101, 223–234.
14) Mims, M. P., et al., (1994) J. Biol. Chem. 269, 20539–20647.
15) Braddock. D. T., et al., (1996) Biochemistry 35, 13975–13984.
16) Venkatachalapathi, Y. V., et al., (1993) Proteins: Structure, Function and Genetics 15, 349–359.
17) Chung, B. H., et al., (1996) J. Lipid Res. 37, 1099–1112
18) Mishra, V. K., et al., (1994) J. Biol. Chem. 269, 7185–7191.
19) Palgunachari, M. N., et al., (1996) Arterio. Thromb. Vasc. Biol. 16,328–338
20) Goldstein, J. L., et al., (1983) Methods Enzymol. 98, 241–260.
21) Bilheimer, et al., (1972) Biochem. Biophys. Acta 260, 212–221.
22) Asztalos, et al., (1993) Biochem. Biophys. Acta 1169, 291–300.
23) Morrisett, J. D., et al., (1973) Biochemistry 12, 1290–1299.
24) Dong, L. M., et al., (1996) Nature Struct. Biol., 3, 718–722.
25) Guilaume, D., et al., 91996) J. Neurochem., 66, 2410–2418.
26) Ji. Z. S., et al., (1994) J. Biol. Chem. 269, 2764–2772.
27) Ji, Z. S., et al., (1993) J. Biol. Chem. 268, 10160–10167.
28) Mahley, R. W., et al., (1979) Biochem. Biophys. Acta 575, 81–89.
29) Al-Haideri, M., et al., (1997) Biochemistry 36, 12766–12772.
30) Garber, D. W., et al., (1997) Circulation, 96, I490.
31) Kieft, K. A., et al., (1991). J. Lipid Res.32, 859–866.
32) Datta, G., et al., (2000) Biochemistry, 39, 213–220.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A synthetic apolipoprotein E-mimicking peptide, consisting of:
   a receptor binding domain of apolipoprotein E selected from the group consisting of any one of SEQ ID NOS: 1–3; and
   a lipid-associating peptide, wherein said receptor binding domain is covalently linked to said peptide.

2. The synthetic apolipoprotein E-mimicking peptide of claim 1, wherein said lipid-associating peptide is model class A amphipathic helical peptide 18A.

3. The synthetic apolipoprotein E-mimicking peptide of claim 1, wherein said apolipoprotein E is from a species selected from the group consisting of human, mouse, rabbit, monkey, rat, bovine, pig and dog.

4. The synthetic apolipoprotein E-mimicking peptide of claim 1, wherein said synthetic peptide is N-terminally protected using acetyl and amino groups.

5. A pharmaceutical composition, comprising the synthetic apolipoprotein E-mimicking peptide of claim 1 and a pharmaceutically acceptable carrier.

6. A method of enhancing low density lipoprotein (LDL) binding to a cell in an individual, comprising the step of:

contacting said cell with the pharmaceutical composition of claim 5, wherein said composition enhances low density lipoprotein binding to said cell.

7. The method of claim 6, wherein said pharmaceutical composition is administered in an amount of about 0.01 mg/kg to about 100 mg/kg.

8. A method of enhancing very low density lipoprotein (VLDL) binding to a cell in an individual, comprising the step of:

contacting said cell with the pharmaceutical composition of claim 5, wherein said composition enhances very low density lipoprotein binding to said cell.

9. The method of claim 8, wherein said pharmaceutical composition is administered in an amount of about 0.01 mg/kg to about 100 mg/kg.

10. A method of increasing low density lipoprotein (LDL) degradation by a cell in an individual, comprising the step of:

contacting said cell with the pharmaceutical composition of claim 5, wherein said composition increasing low density lipoprotein degradation by said cell.

11. The method of claim 10, wherein said pharmaceutical composition is administered in an amount of about 0.01 mg/kg to about 100 mg/kg.

12. A method of increasing very low density lipoprotein (VLDL) degradation by a cell in an individual, comprising the step of:

contacting said cell with the pharmaceutical composition of claim 5, wherein said composition increasing very low density lipoprotein degradation by said cell.

13. The method of claim 12, wherein said pharmaceutical composition is administered in an amount of about 0.01 mg/kg to about 100 mg/kg.

14. A method of lowering low density lipoprotein (LDL) cholesterol in the plasma of an individual in need of such treatment, comprising the step of:

administering the pharmaceutical composition of claim 5 to the bloodstream of said individual, wherein said composition enhances the binding and degradation of said LDL cholesterol by the cells of said individual.

15. The method of claim 14, wherein said pharmaceutical composition is administered in an amount of about. 0.01 mg/kg to about 100 mg/kg.

16. A method of lowering very low density lipoprotein (VLDL) cholesterol the plasma of in an individual in need of such treatment, comprising the step of:

administering the pharmaceutical composition of claim 5 to the bloodstream of said individual, wherein said composition enhances the binding and degradation of said VLDL cholesterol by the cells of said individual.

17. The method of claim 16, wherein said pharmaceutical composition is administered in an amount of about 0.01 mg/kg to about 100 mg/kg.

18. A method of treating an individual with atherosclerosis, comprising the step of:

administering the pharmaceutical composition of claim 5 to the bloodstream of said individual, wherein enhanced binding and degradation of LDL and VLDL cholesterol by the cells of said individual lowers the total plasma concentration of cholesterol in said individual.

19. The method of claim 18, wherein said pharmaceutical composition is administered in an amount of about 0.01 mg/kg to about 100 mg/kg.

* * * * *